United States Patent
Ukon

(10) Patent No.: US 10,359,366 B2
(45) Date of Patent: Jul. 23, 2019

(54) SUBSTRATE FOR SURFACE ENHANCED RAMAN SCATTERING SPECTROSCOPY AND DEVICES USING SAME

(71) Applicant: UKON Craft Science Ltd., Kyoto-shi (JP)

(72) Inventor: Juichiro Ukon, Kyoto (JP)

(73) Assignee: UKON Craft Science Ltd., Kyoto-shi (JP)

(*) Notice: Subject to any disclaimer, the term of this patent is extended or adjusted under 35 U.S.C. 154(b) by 0 days.

(21) Appl. No.: 14/894,159

(22) PCT Filed: Aug. 11, 2014

(86) PCT No.: PCT/JP2014/071164
§ 371 (c)(1),
(2) Date: Nov. 25, 2015

(87) PCT Pub. No.: WO2015/025756
PCT Pub. Date: Feb. 26, 2015

(65) Prior Publication Data
US 2016/0109369 A1    Apr. 21, 2016

(30) Foreign Application Priority Data
Aug. 23, 2013 (JP) .................. 2013-173758

(51) Int. Cl.
*G01N 21/65* (2006.01)
*G01N 30/74* (2006.01)

(52) U.S. Cl.
CPC ........... *G01N 21/658* (2013.01); *G01N 30/74* (2013.01)

(58) Field of Classification Search
CPC .... G01N 21/658; G01N 21/554; B22F 1/0044
See application file for complete search history.

(56) References Cited

U.S. PATENT DOCUMENTS 6,699,724 B1 * 3/2004 West ............... A61K 41/0042
428/403
6,970,239 B2 * 11/2005 Chan .................. C12Q 1/6825
356/301

(Continued)

FOREIGN PATENT DOCUMENTS

JP    2003504642 A    2/2003
JP    2008164584 A    7/2008

(Continued)

OTHER PUBLICATIONS

Richard Walsh, "Silver Coated Porous Alumina as a New Substrate for Surface-Enhanced Raman Scattering", Aug. 2001, Applied Spectrscopy, vol. 55.*

(Continued)

*Primary Examiner* — Maurice C Smith
(74) *Attorney, Agent, or Firm* — The Webb Law Firm

(57) ABSTRACT

It is problematic to provide a substrate for surface enhanced Raman scattering spectroscopy capable of being incorporated and used as a detector of a flow system such as a liquid chromatographic device, and a surface enhanced Raman scattering spectroscopy device and a liquid chromatographic device using same. The above problem is solved by providing a substrate body, pores formed penetrating said substrate body, and particles arranged on an exposed surface of said substrate body not to close the pores, and by an analyte being passed through said particles in-between and said pores.

23 Claims, 8 Drawing Sheets

(56) References Cited

U.S. PATENT DOCUMENTS

| | | | |
|---|---|---|---|
| 7,225,082 B1* | 5/2007 | Natan | B01J 13/0047 257/40 |
| 2001/0002275 A1* | 5/2001 | Oldenburg | A61K 41/0042 427/214 |
| 2003/0228682 A1* | 12/2003 | Lakowicz | G01N 21/6408 435/287.2 |
| 2005/0105085 A1* | 5/2005 | Naya | G01N 21/658 356/301 |
| 2006/0060472 A1* | 3/2006 | Tomita | C25D 11/18 205/112 |
| 2006/0215154 A1* | 9/2006 | Chan | C12Q 1/6825 356/244 |
| 2008/0137081 A1 | 6/2008 | Murakami | |
| 2008/0286526 A1 | 11/2008 | Konakahara | |
| 2010/0035260 A1* | 2/2010 | Olasagasti | C12Q 1/6869 435/6.16 |
| 2010/0291599 A1* | 11/2010 | Tague, Jr. | G01J 3/44 435/7.92 |
| 2011/0249259 A1* | 10/2011 | Van Dorpe | B82Y 15/00 356/301 |
| 2011/0275061 A1 | 11/2011 | Weidemaier et al. | |
| 2011/0311729 A1 | 12/2011 | Sun et al. | |
| 2012/0057163 A1 | 3/2012 | Cheng et al. | |
| 2012/0105841 A1* | 5/2012 | Hu | G01N 21/658 356/301 |
| 2013/0040292 A1* | 2/2013 | Fernandez Lopez | B82Y 15/00 435/6.11 |
| 2014/0104606 A1* | 4/2014 | Shih | G01N 21/658 356/301 |
| 2014/0255500 A1* | 9/2014 | Son | H01L 21/02527 424/490 |
| 2014/0322729 A1 | 10/2014 | Fan et al. | |

FOREIGN PATENT DOCUMENTS

| | | | | |
|---|---|---|---|---|
| JP | 2008168396 A | 7/2008 | | |
| JP | 2008175612 A | 7/2008 | | |
| JP | 2008281529 A | 11/2008 | | |
| JP | 2009150749 A | 7/2009 | | |
| JP | 2010537155 A | 12/2010 | | |
| JP | 201288222 A | 5/2012 | | |
| JP | 2012511705 A | 5/2012 | | |
| JP | 201288222 A1 * | 10/2012 | | G01B 7/00 |
| WO | 2013070948 A1 | 5/2013 | | |

OTHER PUBLICATIONS

Botti et al., "Trace level detection and identification of nitro-based explosives by surface-enhanced Raman spectroscopy", Journal of Raman Spectroscopy, Jan. 2013, pp. 463-468, vol. 44.

Shimada et al., "Near-Field Study on Correlation of Localized Electric Field and Nanostructures in Monolayer Assembly of Gold Nanoparticles", Journal of Physical Chemistry Letters, Feb. 2008, pp. 4033-4035, vol. 112.

Suzuki et al., "Ag nanorod arrays tailored for surface-enhanced Raman imaging in the near-infrared region", Nanotechnology, May 2008, pp. 1-7, vol. 19.

Wu et al., "Electrochemical surface-enhanced Raman spectroscopy of nanostructures", Chemical Society Reviews, Apr. 2008, pp. 1025-1041, vol. 37.

* cited by examiner (a)　　　　　(b)

SUBSTRATE FOR SURFACE ENHANCED RAMAN SCATTERING SPECTROSCOPY AND DEVICES USING SAME

CROSS-REFERENCE TO RELATED APPLICATIONS

This application is the United States national phase of International Application No. PCT/JP2014/071164 filed Aug. 11, 2014, and claims priority to Japanese Patent Application No. 2013-173758 filed Aug. 23, 2013, the disclosure of which are hereby incorporated in their entirety by reference.

TECHNICAL FIELD

This invention relates to a substrate for surface enhanced Raman scattering spectroscopy with pores penetrating the substrate body formed, and a surface enhanced Raman scattering spectroscopy device and a liquid chromatographic device using same.

BACKGROUND ART

When light is irradiated to certain metal microstructures such as metal nanoparticles, the free electrons inside metal resonates with the incident light and causes a collective oscillation, thereby expressing an enhanced electromagnetic field. This phenomenon is known as a Localized Surface Plasmon Resonance (LSPR). This LSPR is especially enhanced in a gap of metal nanoparticle aggregates and the like, and when a molecule absorbs to the gap, the Raman scattering cross-section area of the absorbed molecule is enhanced 10 to the 10th power to 10 to the 14th power compared to the ordinary Raman scattering cross-section area, and a remarkably strong Raman scattering is detected. This approach is called Surface Enhanced Raman Scattering (SERS).

A Raman spectroscopic analysis is a spectroscopic technique used such as in molecular identification of an analyte practiced based on a Raman scattered light generated by irradiating excitation light to the analyte. Since the Raman scattered light is extremely weak, it has an issue that detection is difficult. Accordingly, methods for generating a Raman scattered light with high intensity by using the aforementioned phenomenon called Surface Enhanced Raman Scattering are proposed. The effect of the Raman scattered light being enhanced by SERS (hereinafter called the "SERS effect") is high when the size of the space of the metal particles in-between is of approximately tens of nm or less in size. To obtain such high SERS effect, methods for forming fine spaces in-between the metal particles are variously proposed as shown below.

The substrate for surface enhanced Raman scattering spectroscopy described in nonpatent literature 1 has an inverted pyramidal pit of micron order formed with its inside coated with gold. The SERS effect is produced by granulated gold being adjacent in the bottom part of the pit.

The substrate for surface enhanced Raman scattering spectroscopy described in nonpatent literature 2 has gold covered on a silica columnar layer in a cap like form. The SERS effect is produced by gold placed on each columnar layer being adjacent to each other.

PRIOR ART LITERATURES

Nonpatent Literatures

Nonpatent literature 1: S. Botti, and 5 others, "Trace level detection and identification of nitro-based explosives by surface-enhanced Raman spectroscopy", Journal of Raman Spectroscopy, (US), John Wiley & Sons, Ltd., 25 Jan. 2013, Volume 44, Issue 3, p. 463-468

Nonpatent literature 2: Motofumi Suzuki, and 7 others, "Ag nanorod arrays tailored for surface-enhanced Raman imaging in the near-infrared region", Nanotechnology, (US), IOP Publishing, 19 May 2008, Volume 19, Issue 26, 265304 p. 1-17

DISCLOSURE OF THE INVENTION

Problem to be Solved by the Invention

When a conventional substrate for surface enhanced Raman scattering spectroscopy as described in nonpatent literature 1 and nonpatent literature 2 is used as a part of a detector of a flow system such as a liquid chromatographic device, since an analysis liquid cannot be passed through in a vertical direction to the relevant substrate, the flow direction of the analysis liquid has to be made in a substantially horizontal direction to the relevant substrate. In that case, since only a part of the analyte contacts the particles, the sensitivity is low and the SERS effect cannot be sufficiently obtained. Moreover, since the replacement of the analyte is slow due to the flow velocity being slow at the contact surface with the relevant substrate, there were issues such as an appropriate measurement could not be made. For these reasons, it was extremely difficult to incorporate a surface enhanced Raman scattering spectroscopy device to a flow system such as the liquid chromatographic device.

On this account, as for a liquid chromatographic device, it was necessary to use a Liquid Chromatography Mass Spectrometry (LC-MS) using a Mass Spectrometry (MS) as a detector, or the like, to identify the molecular structure of an analyte. However, since an LC-MS device is an expensive device, it was not a cheap analysis method in obtaining structural information on a daily basis.

The present invention solves the conventional issues as above, and the object of the present invention is to provide a substrate for surface enhanced Raman scattering spectroscopy capable of being incorporated and used as a detector of a flow system such as a liquid chromatographic device, and a surface enhanced Raman scattering spectroscopy device and a liquid chromatographic device using same.

Means for Solving the Problem

The substrate for surface enhanced Raman scattering spectroscopy according to the present invention comprises a substrate body, pores formed penetrating said substrate body, and particles arranged on an exposed surface of said substrate body not to close said pores, wherein said particles are particles in which an analyte is passed through said particles in-between, and said pores are pores in which an analyte is passed through.

The substrate for surface enhanced Raman scattering spectroscopy has said pores being pores in which the analyte passed through said particles in-between passes through.

The substrate for surface enhanced Raman scattering spectroscopy has said particles being particles including gold, silver, copper, platinum, ruthenium, rhodium, palladium, iron, cobalt, or nickel.

The substrate for surface enhanced Raman scattering spectroscopy has said particles being particles in which the surface of a core particle is covered by a metal film.

The substrate for surface enhanced Raman scattering spectroscopy has said particles being particles in which the surface of said core particle is covered by the metal film in a cap like form.

The substrate for surface enhanced Raman scattering spectroscopy has said core particle including silica, alumina, titanium oxide, or polystyrene latex, and said metal film including gold, silver, copper, platinum, ruthenium, rhodium, palladium, iron, cobalt, or nickel.

The substrate for surface enhanced Raman scattering spectroscopy has said particles having an average particle diameter of 10 to 200 nm.

The substrate for surface enhanced Raman scattering spectroscopy has said metal film having an average film thickness of 10 to 200 nm.

The substrate for surface enhanced Raman scattering spectroscopy has said core particle having an average particle diameter of submicron.

The substrate for surface enhanced Raman scattering spectroscopy has said metal film having an average maximum film thickness of 10 to 200 nm.

The substrate for surface enhanced Raman scattering spectroscopy has said particles being particles in which scattered metal particles are adhered to the surface of a non-conductive core particle.

The substrate for surface enhanced Raman scattering spectroscopy has said metal particles having an average particle diameter of 10 to 100 nm.

The substrate for surface enhanced Raman scattering spectroscopy has said metal particles including gold, silver, copper, platinum, ruthenium, rhodium, palladium, iron, cobalt, or nickel.

The substrate for surface enhanced Raman scattering spectroscopy has a conductive coating being performed on the surface of said substrate body to externally adjust the potential of said particles.

The substrate for surface enhanced Raman scattering spectroscopy has said substrate body being an inorganic material.

The substrate for surface enhanced Raman scattering spectroscopy has said substrate body including alumina.

The substrate for surface enhanced Raman scattering spectroscopy has said substrate body being an organic material.

The substrate for surface enhanced Raman scattering spectroscopy has said pores having an average pore diameter smaller than the average particle diameter of said particle and of 5 to 100 nm.

The substrate for surface enhanced Raman scattering spectroscopy has said particles being particles in which the analyte is vertically passed through said particles in-between.

The surface enhanced Raman scattering spectroscopy device has the substrate for surface enhanced Raman scattering spectroscopy as set forth above.

The liquid chromatographic device has the substrate for surface enhanced Raman scattering spectroscopy as set forth above.

The detector of the liquid chromatographic device as set forth above has the substrate for surface enhanced Raman scattering spectroscopy incorporated therein.

Effects of the Invention

According to the substrate for surface enhanced Raman scattering spectroscopy of the present invention, a surface enhanced Raman scattering spectroscopy device can be used as a detector of a flow system such as a liquid chromatograph and the like. Therefore, a Raman scattered light scattered from an analyte and enhanced by SERS is measured in real-time, making the identification and the like of the analyte capable.

EMBODIMENT OF THE INVENTION

A constitution of a substrate for surface enhanced Raman scattering spectroscopy in one embodiment of the present invention will be descried.

Figure 1:
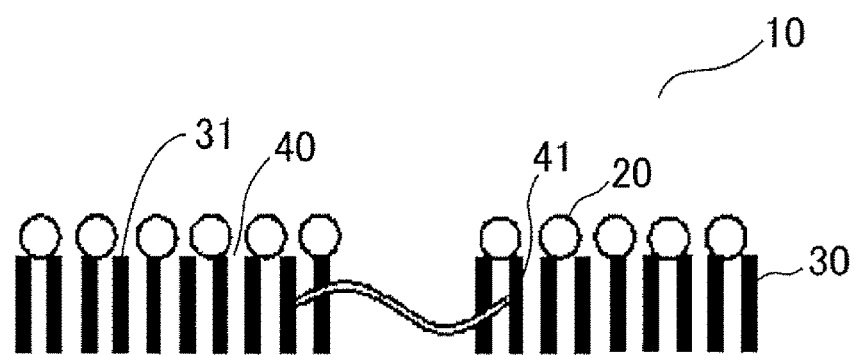
FIG. 1 A conceptual diagram of a substrate for surface enhanced Raman scattering spectroscopy in one embodiment of the present invention.
Figure 2:
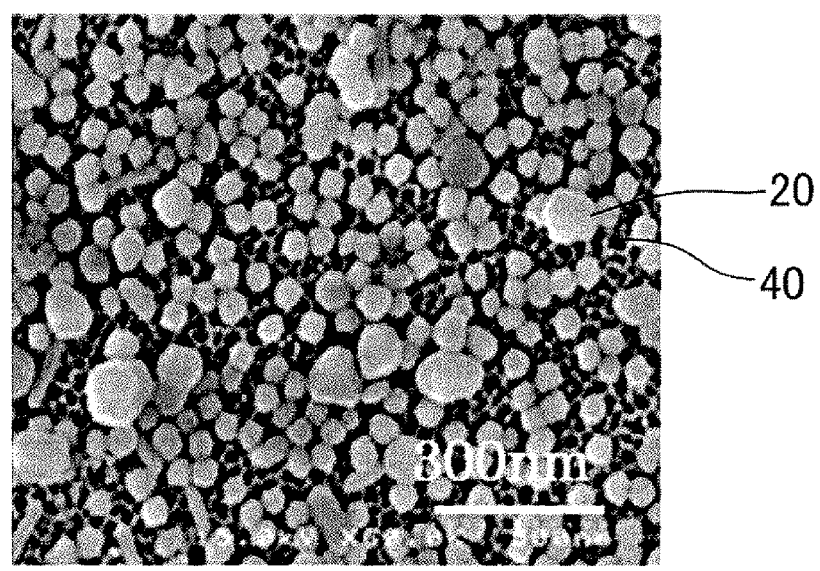
FIG. 2 A figure showing an SEM image of particles and pores of the substrate for surface enhanced Raman scattering spectroscopy in one embodiment of the present invention.

FIG. 1 shows a conceptual diagram of the substrate for surface enhanced Raman scattering spectroscopy in one embodiment of the present invention. FIG. 2 shows an SEM image of particles and pores of the substrate for surface enhanced Raman scattering spectroscopy in one embodiment of the present invention. Furthermore, the scale bar in FIG. 2 shows 300 nm.

As shown in FIG. 1, the substrate for surface enhanced Raman scattering spectroscopy 10 comprises a substrate body 30, pores 40 formed penetrating the substrate body 30, and particles 20 arranged on an exposed surface of the substrate body 30 not to close the pores 40. Furthermore, the exposed surface of a substrate body 30 is a substrate body surface 31 and/or a pore inner wall surface 41 in the range capable of irradiating a measurement light 152 (discussed later).

The particles 20 are preferably particles 20 in which an analyte is vertically passed through said particles 20 in-between. This is because when the analyte and the particles 20 are in such a relation, all the analyte passes through the particles 20 in-between in the range the measurement light 152 is irradiated, so high sensitivity and high responsiveness can be obtained.

The particle 20 is a particle for surface enhanced Raman scattering. Moreover, as shown in FIG. 2, in obtaining the SERS effect, the particles 20 are preferably in plural number, and the particles 20 are preferably adhered or adjacent within tens of nm to each other. The particles 20 according to the present example are gold particles, but it may be particles including other metal, for example, other than gold, particles including silver, copper, or platinum are suitable for obtaining the SERS effect. Moreover, the average particle diameter of the particles 20 is preferably 10 to 200 nm, more preferably 30 to 100 nm. An excellent SERS effect can be obtained in these ranges. Furthermore, the particle diameter, as shown in FIG. 2, is preferable to be scattered to some extent, moreover the particles 20 are preferably adjacent within tens of nm being scattered to some extent rather than adhered. This is because the excellent SERS effect can be obtained by this (reference: Toru Shimada, and 4 others, "Near-Field Study on Correlation of Localized Electric Field and Nanostructures in Monolayer Assembly of Gold Nanoparticles", The Journal of Physical Chemistry C, ACS Publications, Feb. 28, 2008, Volume 112, Issue 11, p.4033-4035). Here, the average particle diameter indicates a number average particle diameter, and the particle diameter (the mean value of the major axis and the minor axis) of at least 1,000 or more particles are measured from a scanning electron microscope (SEM) image and the mean value of them are considered as the average particle diameter.

Figure 3:
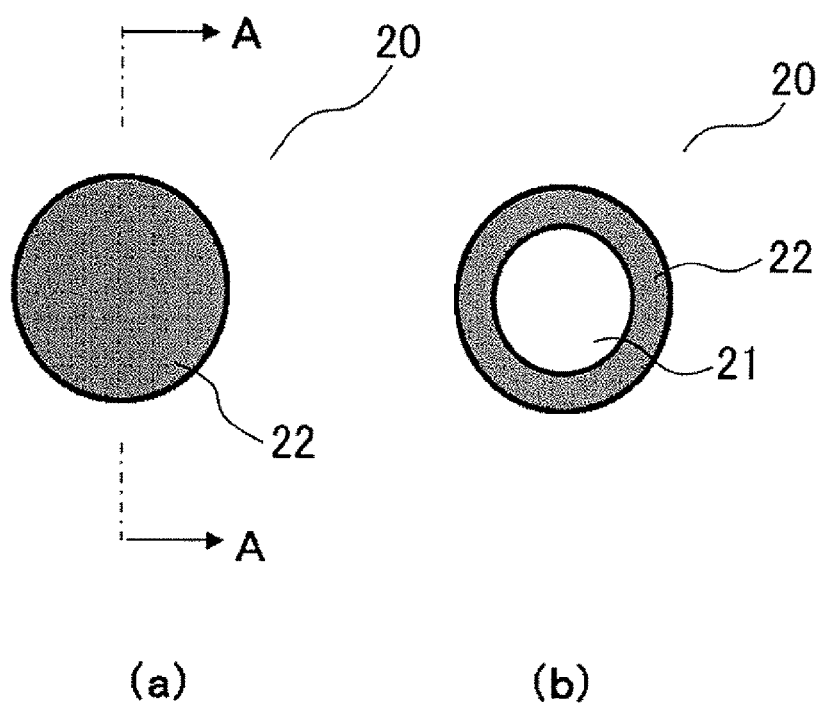
FIG. 3 (a) is a conceptual diagram of a core particle and a metal film of the substrate for surface enhanced Raman scattering spectroscopy in one embodiment of the present invention. (b) is an A-A line cross-sectional schematic diagram.

FIG. 3(a) shows a conceptual diagram of a core particle and a metal film of the substrate for surface enhanced Raman scattering spectroscopy in one embodiment of the present invention. FIG. 3(b) shows an A-A line cross-sectional schematic diagram.

The particles 20, as shown in FIG. 3(a) (b), may be particles in which the surface of the core particle 21 is covered by the metal film 22. For example, silica (SiO2) for the core particle 21, and gold (Au) for the metal film 22 may be used. These particles 20 can be formed by the following manufacturing method and the like. First, the silica particle used as the core particle 21 is formed by a Stober method. Gold nanoparticles protected by tetra-hydroxymethyl phosphonium chloride (THPC) are covered to this silica particle (pre growth solution). By reacting this with a growth solution including gold ions, the growth of the metal film 22 is promoted using gold nanoparticles as seeds, and the particle 20 in which the core particle 21 is covered by the metal film 22 can be formed. For the core particle 21, besides silica, alumina (Al2O3), titanium oxide (TiO2), or polystyrene latex and the like may be used, and for the metal film 22, besides gold, silver, copper, or platinum and the like may be used. The average particle diameter of the core particle 21 is preferably of submicron. Moreover, the average film thickness of the metal film is preferably 10 to 200 nm. Here, the average particle diameter of the core particle indicates a number average particle diameter, and the particle diameter (the mean value of the major axis and the minor axis) of at least 1,000 or more core particles are measured from an SEM image photographing the cross-section of the central part of the particle cut by a microtome and the like and the mean value of them are considered as the average particle diameter of the core particles. Moreover, the average film thickness of the metal film indicates a number average film thickness, and the film thickness (the mean value of the maximum film thickness and the minimum film thickness) of at least 1,000 or more metal films are measured from an SEM image photographing the cross-section of the central part of the particle cut by a microtome and the like and the mean value of them are considered as the average film thickness of the metal film.

Figure 4:
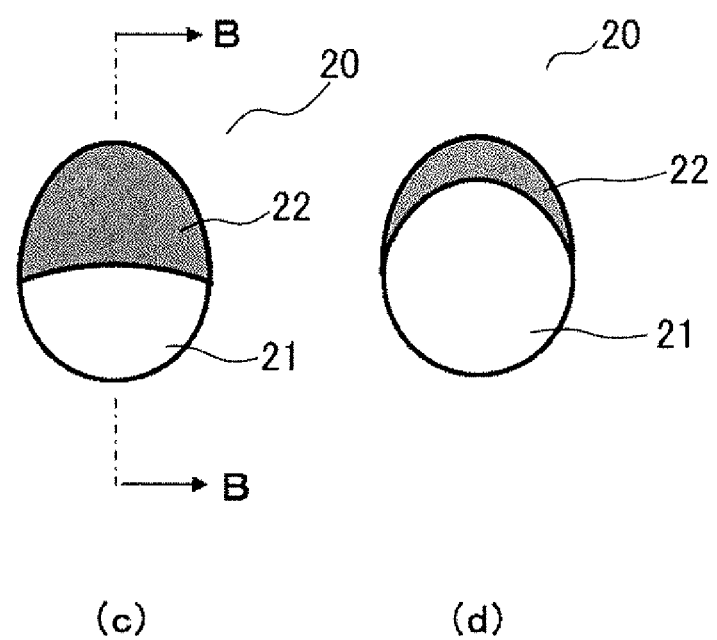
FIG. 4 (c) is a conceptual diagram of the core particle and the metal film covered in a cap like form of the substrate for surface enhanced Raman scattering spectroscopy in one embodiment of the present invention. (d) is a B-B line cross-sectional schematic diagram.

FIG. 4(c) shows a conceptual diagram of the core particle and the metal film covered in a cap like form of the substrate for surface enhanced Raman scattering spectroscopy in one embodiment of the present invention. FIG. 4(d) shows a B-B line cross-sectional schematic diagram.

Further, as shown in FIG. 4(c) (d), the particles 20 may be particles in which the surface of said core particle 21 is covered by the metal film 22. For example, silica (SiO2) for the core particle 21, and gold (Au) for the metal film 22 may be used. As these manufacturing methods, there is a vacuum deposition method or a sputtering method and the like as disclosed such as in Japanese unexamined patent application publication No. 2012-088222. For the core particle 21, besides silica, alumina (Al2O3), titanium oxide (TiO2), or polystyrene latex and the like may be used, and for the metal film 22, besides gold, silver, copper, or platinum and the like may be used. The average maximum film thickness of the metal film is preferably 10 to 200 nm. Here, the average maximum film thickness of the metal film indicates a number average film thickness, and the maximum film thickness of at least 1,000 or more metal films are measured from an SEM image photographing the cross-section of the central part of the particle cut by a microtome and the like and the mean value of them are considered as the average maximum film thickness of the metal film.

Figure 5:
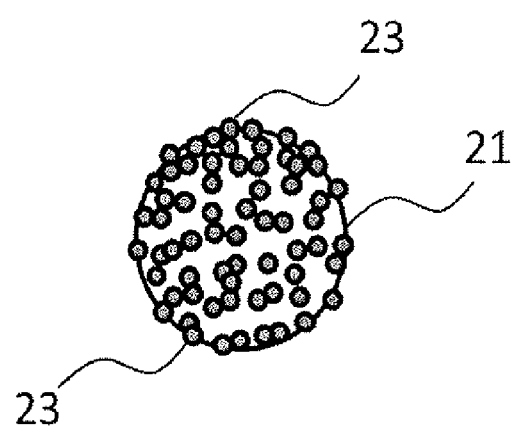
FIG. 5 A conceptual diagram of the core particle and metal particles of the substrate for surface enhanced Raman scattering spectroscopy in one embodiment of the present invention.

FIG. 5 shows a conceptual diagram of the core particle and the metal particles of the substrate for surface enhanced Raman scattering spectroscopy in one embodiment of the present invention.

Moreover, the particles 20 may be particles in which scattered metal particles 23 are adhered to the surface of a non-conductive core particle 21. By adhering scattered metal particles 23 to the surface of the core particle 21, the independent metal particles 23 become adjacent to each other, and many hotspots are caused. Therefore, measurement with even higher sensitivity becomes possible. When the metal particles 23 include gold, silver, copper, platinum, ruthenium, rhodium, palladium, iron, cobalt, or nickel, it is preferable for obtaining the SERS effect. A defined particle diameter is preferably used as that of the metal particles 23. By this, since the quantity and quality of the hotspot becomes uniform, a stable SERS effect can be produced. The average particle diameter of the metal particles 23 is preferably 10 to 100 nm. Here, the average particle diameter indicates a number average particle diameter, and the particle diameter (the mean value of the major axis and the minor axis) of at least 1,000 or more particles are measured from an SEM image and the mean value of them are considered as the average particle diameter. When the core particle 21 is a non-conductor, it is preferable since the core particle does not inhibit the SERS effect caused by the metal particles.

Figure 6:
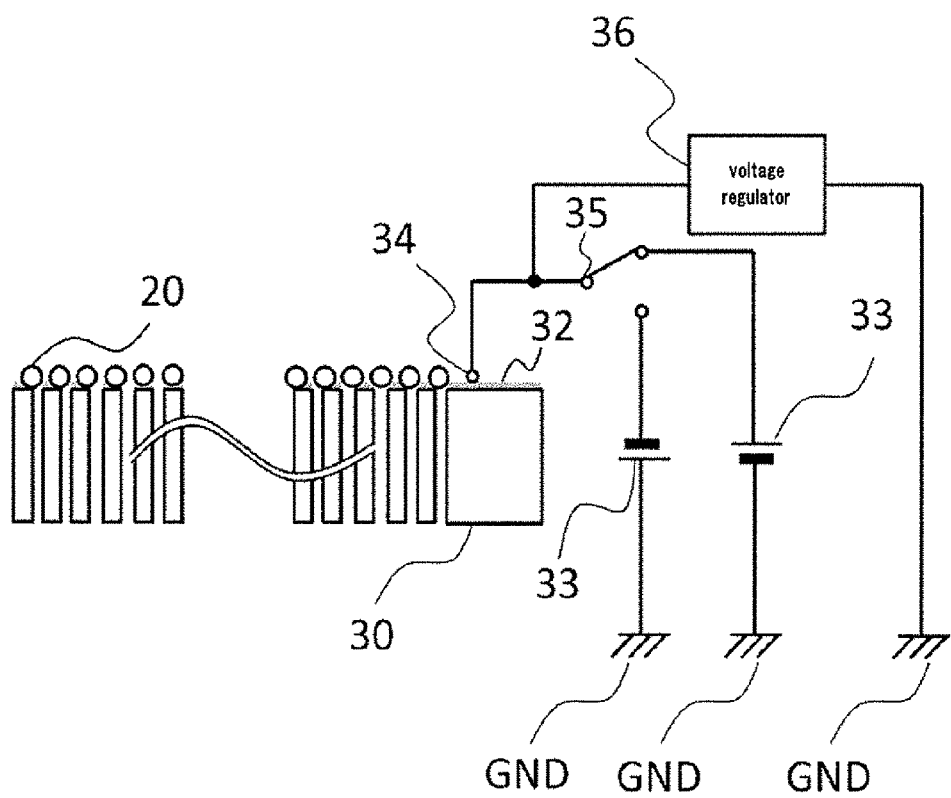
FIG. 6 A constitution diagram when a conductive coating is performed on the substrate for surface enhanced Raman scattering spectroscopy in one embodiment of the present invention.

FIG. 6 shows a constitution diagram when a conductive coating is performed on the substrate for surface enhanced Raman scattering spectroscopy in one embodiment of the present invention.

The conductive coating 32 is performed on the surface of the substrate body 30 of FIG. 6 to externally adjust the potential of the particles 20, and an electrode 34 is connected to the conductive coating 32, and a voltage regulator 36, a switch 35, a power source 33, a ground is connected from the electrode 34. Since the power source to be used can be changed by switching the switch 35, a negative potential or a positive potential can be applied to the particles 20 as necessary. Moreover, the potential of the particles 20 can be adjusted by the voltage regulator 36. The voltage regulator 36 can adjust the potential by having a variable resistor or the like in its inside. Furthermore, the potential of the analyte itself is ground level.

Two effects are caused by said constitution making it possible to adjust the potential of the particles 20 externally.

The first is that a high sensitivity measurement can be made. For example, when the analyte is a cationic molecule, since more molecules of the analyte absorb to the particles 20 by applying the negative potential to the particles 20, a measurement of high sensitivity can be made. Since molecules of the analyte can be released from the particles 20 by applying the positive potential after measurement, issues such as the analyte remaining do not occur.

Similarly, when the analyte is an anionic molecule, more molecules of the analyte absorb to the particles 20 by applying the positive potential to the particles 20, a measurement of high sensitivity can be made. Molecules of the analyte can be released from the particles 20 by applying the negative potential after measurement.

The second is that increasing the Raman scattering intensity becomes capable. Since the potential of the molecules of the analyte adhered to the particles 20 can be adjusted, the ground state of an electron constituting the molecule can be changed. Therefore, when the electron is excited by laser, the transition to one upper energy level produces the same effect as a resonance Raman and the Raman scattering intensity can be increased (reference: De-Yin Wu, and 3 others, "Electrochemical surface-enhanced Raman spectroscopy of nanostructures", Chemical Society Reviews, Royal Society of Chemistry, 3 Apr. 2008, Volume 37, 2008 Issue 5, p.1025-1041).

Furthermore, although the conductive coating 32 includes metal coating, it is not limited thereto.

An inorganic material may be used for the substrate body 30. Alumina (Al2O3) is especially preferable. This is because since alumina does not have a characteristic Raman spectrum, when used for the substrate body 30, it seldom hinders the detection and analysis of the Raman spectrum of the analyte. On the other hand, an organic material may also be used for the substrate body 30. For example, a resin film and the like may be used. Since an organic material has a characteristic Raman spectrum, data processing and the like has to be done in advance not to hinder the detection and analysis of the Raman spectrum of the analyte. By this, an organic material may be used for the substrate body 30.

The pores 40 formed penetrating the substrate body 30 can be prepared by the following manufacturing method. When the substrate body 30 is an inorganic material, for example alumina, pores 40 of nano order can be prepared by anodization of aluminum. When the substrate body 30 is an organic material, for example a resin film, pores 40 of nano order can be prepared by irradiating neutron radiation to the resin film. The pores 40 preferably have an average pore diameter smaller than the average particle diameter of the particles 20. This is because when the average pore diameter of the pores 40 become larger than the average particle diameter of the particles 20, the flow out of the particles 20 together with the analyte and the like from the pores 40 increases at the time the analyte and the like passes through the particles 20 in-between and the pores 40. Further, the pores 40 preferably have the average pore diameter of 5 to 100 nm. Moreover, as shown in FIG. 2, the pores 40 preferably exist in plural, but pores 40 without particles 20 arranged on the upper surface or the vicinity of the upper surface of the pore 40 may be included. This is because though the SERS effect is hard to obtain near these pores 40, there is no problem if the SERS effect is obtained in the whole range the measurement light 152 (discussed later) is irradiated. Here, the average pore diameter indicates a number average pore diameter, and the pore diameter (the mean value of the major axis and the minor axis) of at least 1,000 or more particles are measured from an SEM image and the mean value of them are considered as the average pore diameter.

To arrange particles 20 on an exposed surface of the substrate body 30, a suspension with gold nanoparticles and the like dispersed in a liquid should be passed through the pores 40 and dried. The number of particles 20 to be arranged on the exposed surface of the substrate body 30 can be freely controlled by the concentration of the suspension measured with an absorption photometer and the like and the liquid measure of the suspension passing through the pores 40.

Next, the constitution of a liquid chromatographic device and a surface enhanced Raman scattering spectroscopy device used as its detector in one embodiment of the present invention will be descried.

Figure 7:
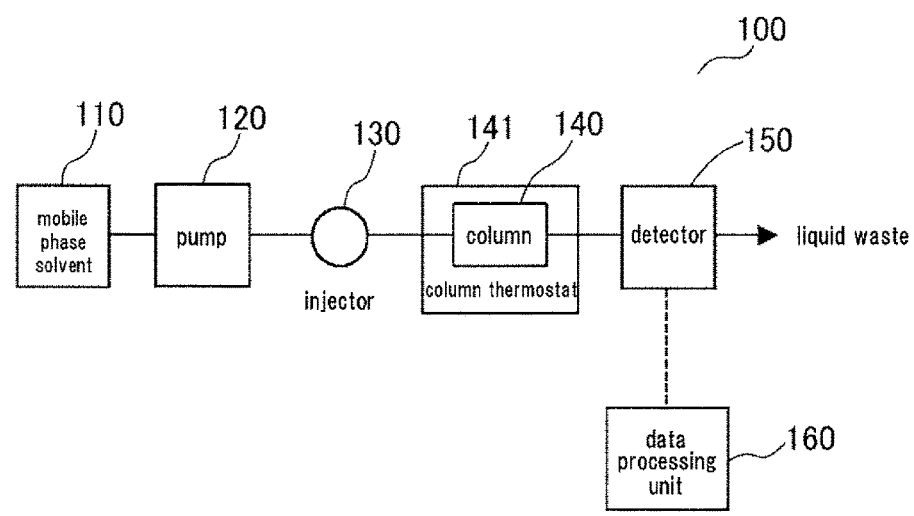
FIG. 7 A constitution diagram of a liquid chromatographic device in one embodiment of the present invention.

FIG. 7 shows a constitution diagram of the liquid chromatographic device in one embodiment of the present invention.

As shown in FIG. 7, the liquid chromatographic device 100 in the embodiment of the present invention comprises a mobile phase solvent 110, a pump 120, an injector 130, a column 140, a column thermostat 141, a detector 150, and a data processing unit 160. The surface enhanced Raman scattering spectroscopy device is incorporated as the detector 150.

Figure 8:
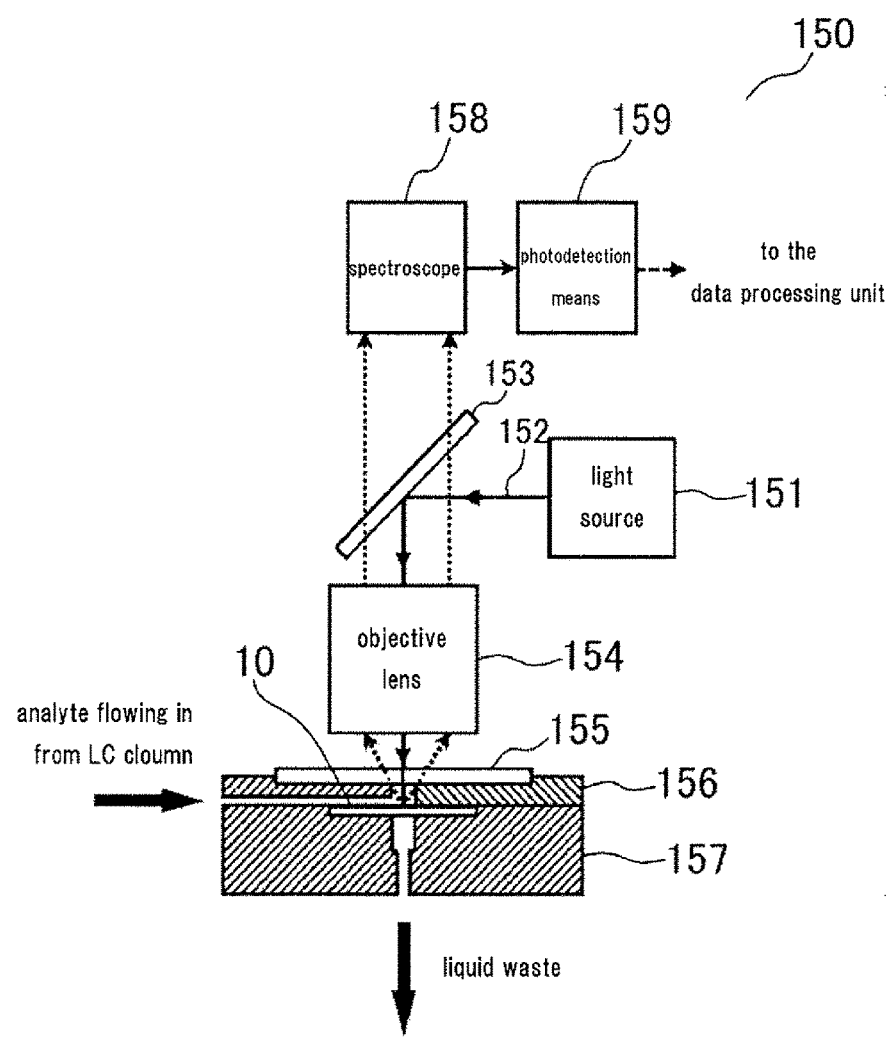
FIG. 8 A schematic diagram of a surface enhanced Raman scattering spectroscopy device used as a detector of the liquid chromatographic device in one embodiment of the present invention.

FIG. 8 shows a schematic diagram of the surface enhanced Raman scattering spectroscopy device used as the detector of the liquid chromatographic device in one embodiment of the present invention.

As shown in FIG. 8, the surface enhanced Raman scattering spectroscopy device used as the detector 150 in one embodiment of the present invention comprises a light source 151, a transmission reflection part 153, an objective lens 154, a transparent plate 155, an opening/closing part 156, a base part 157, a spectroscope 158, a photodetection means 159, and the substrate for surface enhanced Raman scattering spectroscopy 10.

The light source 151 generates the measurement light 152 such as laser. The objective lens 154 narrows down the measurement light 152 and irradiate the analyte, and condense the Raman scattered light scattered from the analyte. The transmission reflection part 153 reflects the measurement light 152 generated from the light source 151 and transmits the Raman scattered light condensed by the objective lens. A beam splitter or a dichroic mirror can be used as the transmission reflection part 153. The photodetection means 159 such as a camera detects the Raman scattered light which passed through the spectroscope 158.

Hereinafter, the operation of the liquid chromatographic device and the surface enhanced Raman scattering spectroscopy device used as its detector in one embodiment of the present invention will be descried.

The measurement light 152 generated from the light source 151 is reflected by the transmission reflection part 153, transmits the transparent plate 155, and is irradiated to the substrate for surface enhanced Raman scattering spectroscopy 10. The analyte is flowing into the substrate for surface enhanced Raman scattering spectroscopy 10 from the column 140 of the liquid chromatographic device 100, and the measurement light 152 is irradiated to the analyte and the particles 20 arranged on the exposed surface of the substrate body 30. And then, the Raman scattered light scattered from the analyte transmits the transparent plate 155 and is condensed by the objective lens 154 after being enhanced by the SERS effect. The Raman scattered light condensed by the objective lens 154 is transmitted by the transmission reflection part 153, and after passing through the spectroscope 158, the Raman scattered light is detected by the photodetection means 159. The detection result is transmitted to the data processing unit 160 by an electrical signal or the like and data processing, visualization and the like is practiced. Based on the result of the data processing, identification and the like of the analyte can be practiced.

On the other hand, the analyte flown into the substrate for surface enhanced Raman scattering spectroscopy 10 from the column 140 passes through the particles 20 in-between and the pores 40, and subsequently is discharged as liquid waste. Furthermore, when particles 20 are arranged on the upper surface of the substrate body 30, the analyte passes through the pores 40 after passing through the particles 20 in-between.

Since the analyte separated in the column 140 hardly keeps absorbing to the particles 20, it is not necessary to clean/exchange, etc. the substrate for surface enhanced Raman scattering spectroscopy 10 for each separated analyte. Therefore, measurement of the analyte successively flowing in in real time becomes possible.

Moreover, in exchanging the substrate for surface enhanced Raman scattering spectroscopy 10, it can be easily attached or detached by opening and closing the opening/closing part 156.

Incidentally, not only to the detector 150 of the liquid chromatographic device 100, but the substrate for surface enhanced Raman scattering spectroscopy 10 according to the present invention can also be incorporated to the conventional surface enhanced Raman scattering spectroscopy device such as nonpatent literature 1 and 2. In that case, it becomes possible to be used plurality of times by cleaning the substrate for surface enhanced Raman scattering spectroscopy 10 using a cleaning solution and the like.

EXPLANATION OF REFERENCES 10 substrate for surface enhanced Raman scattering spectroscopy
20 particle
21 core particle
22 metal film
23 metal particle
30 substrate body
31 substrate body surface
32 conductive coating
33 power source
34 electrode
35 switch
36 voltage regulator
GND ground
40 pore
41 pore inner wall surface
100 liquid chromatographic device
110 mobile phase solvent
120 pump
130 injector
140 column
141 column thermostat
150 detector
151 light source
152 measurement light
153 transmission reflection part
154 objective lens
155 transparent plate
156 opening/closing part
157 base part
158 spectroscope
159 photodetection means
160 data processing unit

What is claimed is:

1. A substrate for surface enhanced Raman scattering spectroscopy incorporated as a detector of a liquid flow system, wherein said substrate comprises:
a porous substrate body having numerous pores which are penetrating said substrate body and arranged in parallel, numerous particles arranged on an exposed surface of said substrate body so as not to close said pores, wherein said particles are adjacent to one another within tens of nanometers, and numerous nanogaps between said particles having SERS sensitivity developed on said porous substrate body,
wherein said pores have an average pore diameter that is smaller than an average particle diameter of said particles, and
wherein an analyte of a liquid passes through said nanogaps and through said pores of said porous substrate body in a vertical direction to the substrate body, is discharged from said pores.

2. The substrate for surface enhanced Raman scattering spectroscopy as set forth in claim 1, wherein said particles are particles including gold, silver, copper, platinum, ruthenium, rhodium, palladium, iron, cobalt, or nickel.

3. The substrate for surface enhanced Raman scattering spectroscopy as set forth in claim 1, wherein each of said particles comprises a core particle wherein a surface of said core particle is covered by a metal film.

4. The substrate for surface enhanced Raman scattering spectroscopy as set forth in claim 3, wherein said particles are particles in which the surface of said core particle is covered by the metal film in a cap like form.

5. The substrate for surface enhanced Raman scattering spectroscopy as set forth in claim 3, wherein said core particle includes silica, alumina, titanium oxide, or polystyrene latex, and
said metal film includes gold, silver, copper, platinum, ruthenium, rhodium, palladium, iron, cobalt, or nickel.

6. The substrate for surface enhanced Raman scattering spectroscopy as set forth in claim 2, wherein said particles have an average particle diameter within the range of 10 to 200 nm.

7. The substrate for surface enhanced Raman scattering spectroscopy as set forth in claim 3, wherein said metal film has an average film thickness within the range of 10 to 200 nm.

8. The substrate for surface enhanced Raman scattering spectroscopy as set forth in claim 3, wherein said core particle has an average particle diameter of submicron.

9. The substrate for surface enhanced Raman scattering spectroscopy as set forth in claim 3, wherein said metal film has an average maximum film thickness within the range of 10 to 200 nm.

10. The substrate for surface enhanced Raman scattering spectroscopy as set forth in claim 1, wherein each of said particles comprises a non-conductive core particle and scattered metal particles adhered to a surface of the non-conductive core particle.

11. The substrate for surface enhanced Raman scattering spectroscopy as set forth in claim 10, wherein said metal particles have an average particle diameter within the range of 10 to 100 nm.

12. The substrate for surface enhanced Raman scattering spectroscopy as set forth in claim 10, wherein said metal particles include gold, silver, copper, platinum, ruthenium, rhodium, palladium, iron, cobalt, or nickel.

13. The substrate for surface enhanced Raman scattering spectroscopy as set forth in claim 1, wherein a conductive coating is performed on the surface of said substrate body to externally adjust the potential of said particles.

14. The substrate for surface enhanced Raman scattering spectroscopy as set forth in claim 1, wherein said substrate body is an inorganic material.

15. The substrate for surface enhanced Raman scattering spectroscopy as set forth in claim 14, wherein said substrate body includes alumina.

16. The substrate for surface enhanced Raman scattering spectroscopy as set forth in claim 1, wherein said substrate body is an organic material.

17. The substrate for surface enhanced Raman scattering spectroscopy as set forth in claim 1, wherein said average pore diameter is within the range of 5 to 100 nm.

18. A surface enhanced Raman scattering spectroscopy device, wherein the substrate for surface enhanced Raman scattering spectroscopy as set forth in claim 1 is incorporated.

19. A liquid chromatographic device, wherein the substrate for surface enhanced Raman scattering spectroscopy as set forth in claim 1 is incorporated.

20. A detector of the liquid chromatographic device, wherein the substrate for surface enhanced Raman scattering spectroscopy as set forth in claim 1 is incorporated.

21. The substrate for surface enhanced Raman scattering spectroscopy as set forth in claim 1, wherein said average pore diameter is within the range of 5 to 100 nm, and
wherein said particles have scattered particle diameters which the average particle diameter is within the range of 10 to 200 nm.

22. The substrate for surface enhanced Raman scattering spectroscopy as set forth in claim 1, including pores without particles arranged on the upper surface or the vicinity of the upper surface of the pore.

23. The substrate for surface enhanced Raman scattering spectroscopy as set forth in claim 1, wherein particles are adhered to each other.

* * * * *